(12) United States Patent
Hatley et al.

(10) Patent No.: US 6,222,897 B1
(45) Date of Patent: Apr. 24, 2001

(54) WRIST RASTER SCAN METHODS

(75) Inventors: Richard M. Hatley, Madison, NJ (US); Terry S. Rockwood, Lakeland, FL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/139,547

(22) Filed: Aug. 25, 1998

Related U.S. Application Data

(60) Provisional application No. 60/079,430, filed on Feb. 27, 1998.

(51) Int. Cl.$^7$ .......................... G21C 17/017; G01N 29/00
(52) U.S. Cl. .......................... 376/245; 376/249; 376/252; 73/622; 73/637; 73/638; 73/866.5
(58) Field of Search ..................................... 376/245, 249, 376/252; 73/622, 637, 638, 866.5

(56) References Cited

U.S. PATENT DOCUMENTS

| | | | |
|---|---|---|---|
| 4,131,018 | * 12/1978 | Muller et al. | 376/249 |
| 4,416,846 | * 11/1983 | Kastl | 376/249 |
| 4,515,018 | * 5/1985 | Kajiyama | 73/637 |
| 4,672,852 | * 6/1987 | Gugel et al. | 376/245 |
| 5,118,462 | * 6/1992 | Dirauf et al. | 376/249 |

FOREIGN PATENT DOCUMENTS 11-109081 * 4/1999 (JP) ...................................... 376/245

* cited by examiner

*Primary Examiner*—Michael J. Carone
*Assistant Examiner*—Jack Keith
(74) *Attorney, Agent, or Firm*—Armstrong Teasdale LLP

(57) ABSTRACT

Scan methods of inspecting piping and welds of a pipe elbow in a reactor pressure vessel of a boiling water reactor are disclosed. The scan apparatus includes a motor connected to a scan head having two ultrasonic transducer probes each including an ultrasonic transducer, a transducer arm connected to each transducer probe, a scan platform having an arcuate cutout, and a connector connecting each transducer arm to the scan platform. The scan head allows the transducer probes to remain substantially in contact with the pipe elbow while the scan head traverses the pipe elbow. The scan apparatus further includes a pivot arm connecting the scan platform to a pivot pin. The method includes the steps of positioning the scan head and the transducer probe such that the ultrasonic transducer is substantially in contact with the pipe elbow surface. Then moving the scan head axially along the pipe elbow in a first direction while maintaining the ultrasonic transducer in substantial contact with the pipe elbow surface. Then incrementally rotating the probes, in a raster type manner, and moving the scan head axially along the pipe elbow in a second direction. The steps are repeated until the entire pipe elbow surface has been inspected.

14 Claims, 4 Drawing Sheets

WRIST RASTER SCAN METHODS

CROSS REFERENCE TO RELATED APPLICATION

This application claims the benefit of U.S. Provisional Application No. 60/076,430, filed Feb. 27, 1998.

FIELD OF THE INVENTION

This invention relates generally to nuclear reactors and, more particularly, to methods and apparatus for inspecting core spray and jet pump riser inlet piping.

BACKGROUND OF THE INVENTION

A reactor pressure vessel of a boiling water reactor typically has numerous piping systems. Such piping systems are utilized, for example to transport water throughout the reactor pressure vessel. For example, core spray piping delivers water to a reactor core.

Over the life of the reactor, the piping is often inspected to verify integrity. For example, the piping welds must be periodically inspected for Inter Granular Stress Corrosion Cracking (IGSCC). Based upon such inspections, the piping may require either repair or replacement.

Problems arise when attempting to inspect small or tight radius elbows on small diameter core spray piping and jet pump riser inlet piping systems, using volumetric ultrasonic techniques. Known pipe inspecting apparatus may not be able to sufficiently cover pipe elbow weld areas for volumetric ultrasonic examinations because of an inability to maintain ultrasonic transducer contact with the surface to be examined.

It would be desirable to provide an easy to use pipe inspection apparatus and methods for inspecting nuclear reactor piping. Preferably, the apparatus and methods would utilize a motion that more readily conforms to the contours of the pipe elbows. It would also be desirable to facilitate maintaining ultrasonic transducers of the inspection apparatus in sufficient contact with the surface of the piping being inspected to allow the ultrasonic transducers to produce accurate scan readings.

SUMMARY OF THE INVENTION

These and other objects may be attained by apparatus for inspecting piping and welds of pipe elbows in a reactor pressure vessel of a boiling water reactor which, in one embodiment, includes a scan head having a pair of spaced apart ultrasonic transducer probes and a motor that moves the scan head axially along the pipe elbow. The scan head allows the transducer probes to remain substantially in contact with the pipe elbow while the scan head traverses the pipe elbow. The ultrasonic transducer probes can detect flaws in the piping and the welds of the pipe elbows and are contoured to conform to the piping.

The scan head also includes a scan platform, a connector, and a pair of transducer arms each having a first end and a second end. Each transducer arm first end is connected to one of the transducer probes. The connector attaches the transducer arms to the scan platform and permits the transducer probes to orbit freely about the connector producing a gimbals type movement. The freedom of movement of the transducer probes allows the probes to remain in contact with the pipe elbow. The scan platform includes an arcuate cutout having a size and shape to accommodate the piping. The connector slides along the arcuate cutout. As the connector slides along the cutout, the transducer probes and the transducer arms are caused to rotate, at least partially, about a circumference of the piping.

The inspecting apparatus further includes a pivot arm having a first end and a second end connected to the scanner platform. A pivot pin is connected to the pivot arm first end. The motor pivots the pivot arm second end about the pivot pin. The pivoting of the pivot arm second end causes the transducer probes to pivot substantially about the pivot pin.

A method of inspecting piping and welds of a pipe elbow using the above described scan apparatus includes positioning the scan head and the ultrasonic transducer probes such that the probes are substantially in contact with the pipe elbow surface. The motor is then used to pivot the transducer probes substantially about the pivot pin which allows the transducer probes to travel axially along the pipe elbow while the probes remain in substantial contact with the pipe elbow surface. The scan head, during this pivoting movement, inspects the piping and the welds in the pipe elbow to detect flaws. The scan apparatus moves with a wrist scan motion to enhance the ability of the probes to remain in contact with the pipe elbow surface during the inspection and to enable ultrasonic transducer signals to better penetrate the piping and welds of the pipe elbow. The piping and the weld material of the pipe elbow are inspected as the transducer probes move substantially perpendicular to the weld.

In operation, the scan head moves axially along the pipe elbow in a first direction from a first axial point to a second axial point. The connector then slides along the cutout, incrementally rotating, in a raster type manner, the probes. The scan head then moves axially along the pipe elbow in a second direction from the second axial point to the first axial point. Again, the connector slides along the cutout, incrementally rotating, in a raster type manner, the probes. Each incremental rotation of the probes moves the probes about a partial circumference of the piping. The axial movement of the probes and the incremental rotation at the ends of the axial stroke are repeated until the probes have inspected the entire surface of the pipe elbow.

A method of positioning ultrasonic transducer probes to examine piping and welds of a pipe elbow begins by locating the above described scan apparatus at the pipe elbow. Since the above described scan apparatus is for use in a reactor pressure vessel of a boiling water reactor, the scan apparatus can be deployed in water to a depth of more than about 60 feet. The scan head is then moved to allow at least a portion of the piping to enter the scan platform cutout. After the transducer probes are positioned substantially in contact with the pipe elbow, the scan head is moved axially along the pipe elbow while the transducer probes are maintained in substantial contact with the pipe elbow. The axial movement of the pipe elbow begins at a first axial point and moves in a first direction to a second axial point. The connector is then moved incrementally along the arcuate cutout which causes the transducer probes and the transducer arms to rotate partially about the circumference of the piping. The scan head is then moved axially along the pipe elbow in a second direction from the second axial point to the first axial point. Again, the connector is moved incrementally along the arcuate cutout which causes the transducer probes and the transducer arms to rotate partially about the circumference of the piping. The axial movement of the probes and the incremental rotation at the ends of the axial stroke are repeated until the probes have investigated the entire surface of the pipe elbow.

The above described scan apparatus allows the ultrasonic transducers to remain in contact with the outer surface of the pipe elbow until the entire inspection has been completed. The wrist scan motion enhances the transducers abilities to contour to the piping surface and enable the transducer signals to better penetrate the surface. The wrist scan motion also enhances the signal dynamics of the transducers enabling the operator to discern between geometric reflections and cracks.

DETAILED DESCRIPTION

Figure 1:
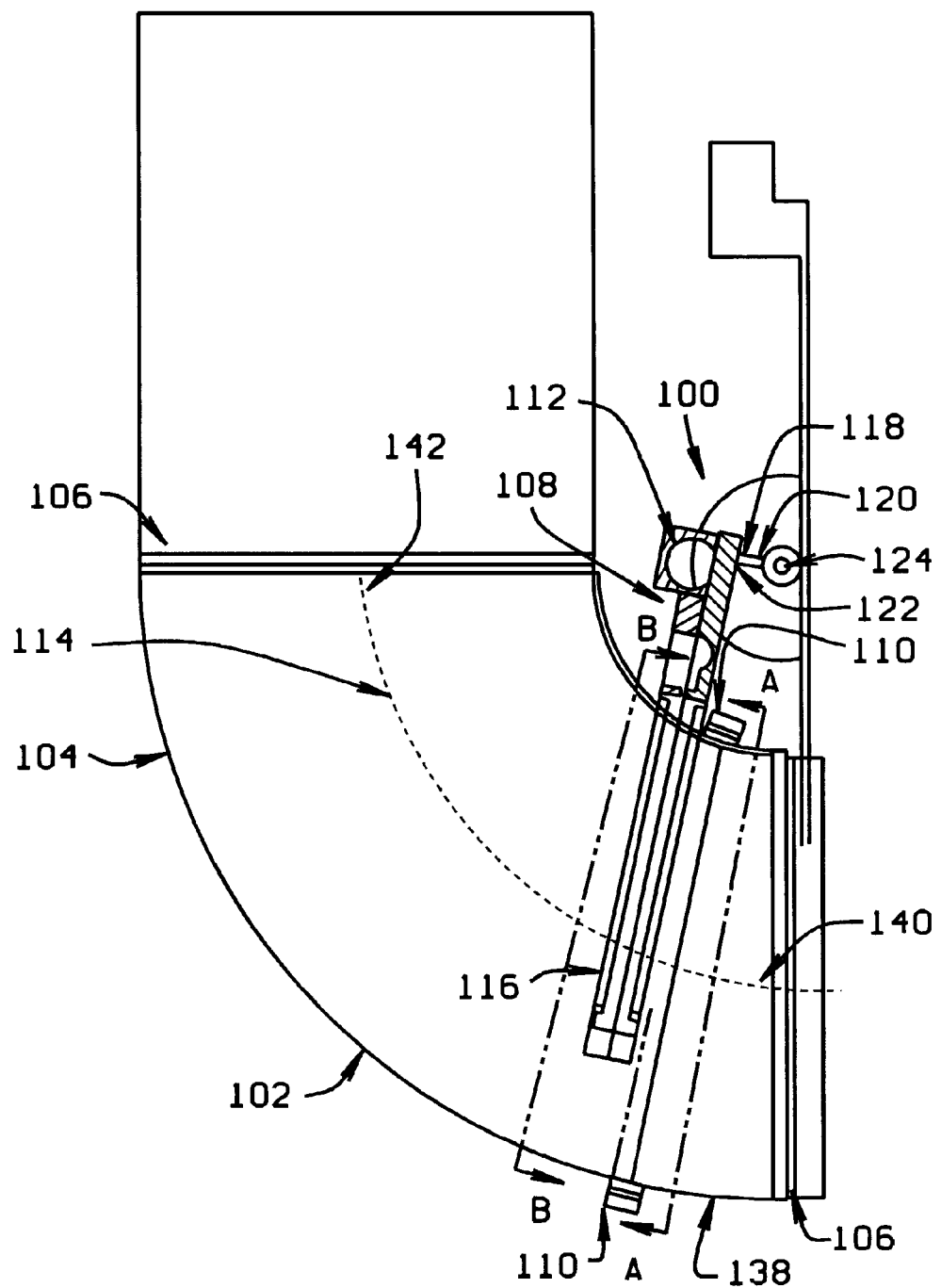
FIG. 1 is a side view of a scan apparatus on a pipe elbow.

FIG. 1 is a side view of a scan apparatus 100 positioned about a pipe elbow 102. Apparatus 100 can inspect piping 104 and welds 106 of pipe elbows 102 in a reactor pressure vessel (not shown) of a boiling water reactor (not shown). Apparatus 100 includes a scan head 108 having at least one ultrasonic transducer 110 and a motor 112 that moves scan head 108 along a pipe elbow axis 114. In one embodiment, scan head 108 includes a pair of spaced apart ultrasonic transducers 110. Scan head 108 allows transducers 110 to remain substantially in contact with pipe elbow 102 while scan head 108 traverses pipe elbow 102. Ultrasonic transducers 110 can detect flaws in piping 104 and welds 106 of pipe elbows 102. Transducers 110 are contoured to conform to piping 104.

Scan apparatus 100 further includes a scan platform 116 and a pivot arm 118 having a first end 120 and a second end 122. Pivot arm 118 connects scan platform 116 to a pivot pin 124. Specifically, pivot arm second end 122 is connected to scan platform 116 and pivot arm first end 120 is connected to pivot pin 124. Motor 112 pivots pivot arm second end 122 about pivot pin 124. The connection of scan head 108 to pivot arm second end 122 allows ultrasonic transducers 110 to pivot substantially about pivot pin 124 when pivot arm second end 122 pivots about pivot pin 124.

Figure 2:
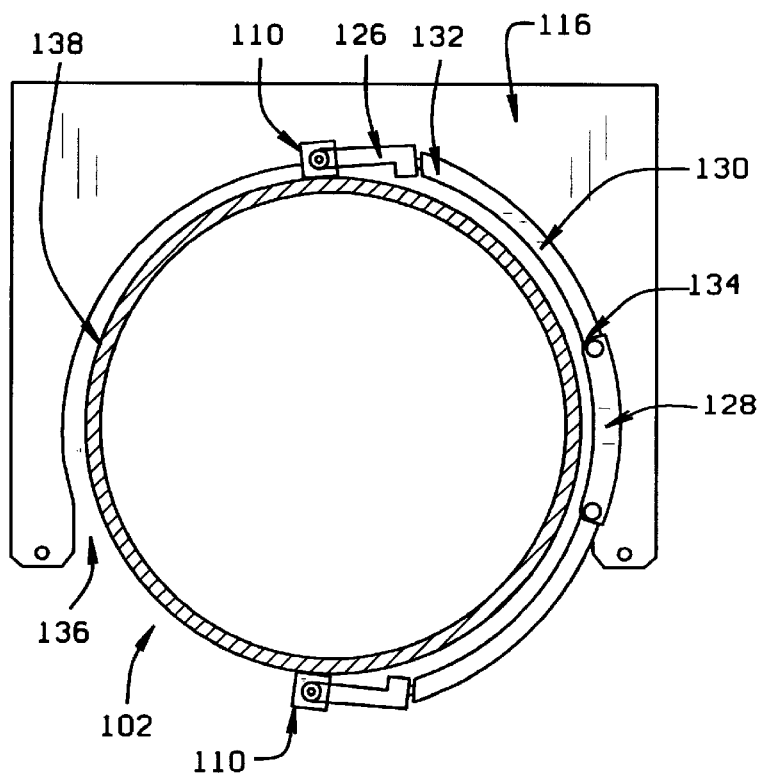
FIG. 2 is a cross section of the pipe elbow shown in FIG. 1 along A—A including a bottom view of the scan apparatus shown in FIG. 1.
Figure 3:
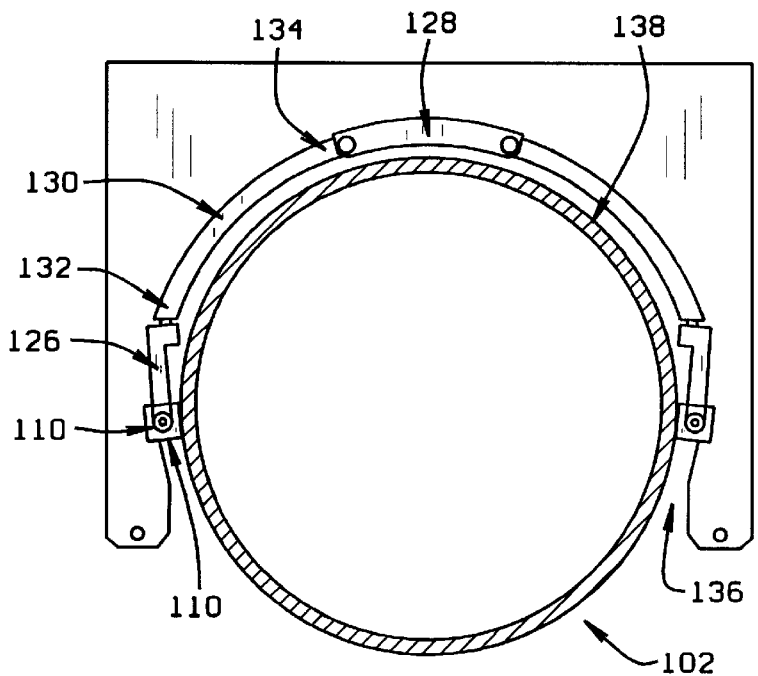
FIG. 3 is a bottom view of the scan apparatus and pipe elbow shown in FIG. 2 having a pair of ultrasonic transducer probes rotated about 90 degrees.

FIGS. 2 and 3 are bottom views of scan apparatus 100 including a pair of transducer probes 126 including ultrasonic transducers 110, a connector 128, and a pair of transducer arms 130 each having a first end 132 and a second end 134. Each transducer arm first end 132 is connected to one of transducer probes 126. Connector 128 connects both transducer arm second ends 134 to scan platform 116 which is connected to motor 112. Connector 128, transducer arms 130, and transducer probes 126 form a gimbals that allows ultrasonic transducers 110 to orbit freely about scan platform 116. This freedom of movement of ultrasonic transducers 110 allows ultrasonic transducers 110 to remain in contact with pipe elbow 102 throughout the movement of scan head 108 along pipe elbow 102. Scan platform 116 includes an arcuate cutout 136 having a size and shape to accommodate piping 104. Connector 128 slides along arcuate cutout 136. As connector 128 slides along cutout 136, ultrasonic transducers 110 rotate, at least partially, about a circumference of piping 104.

Figure 4:
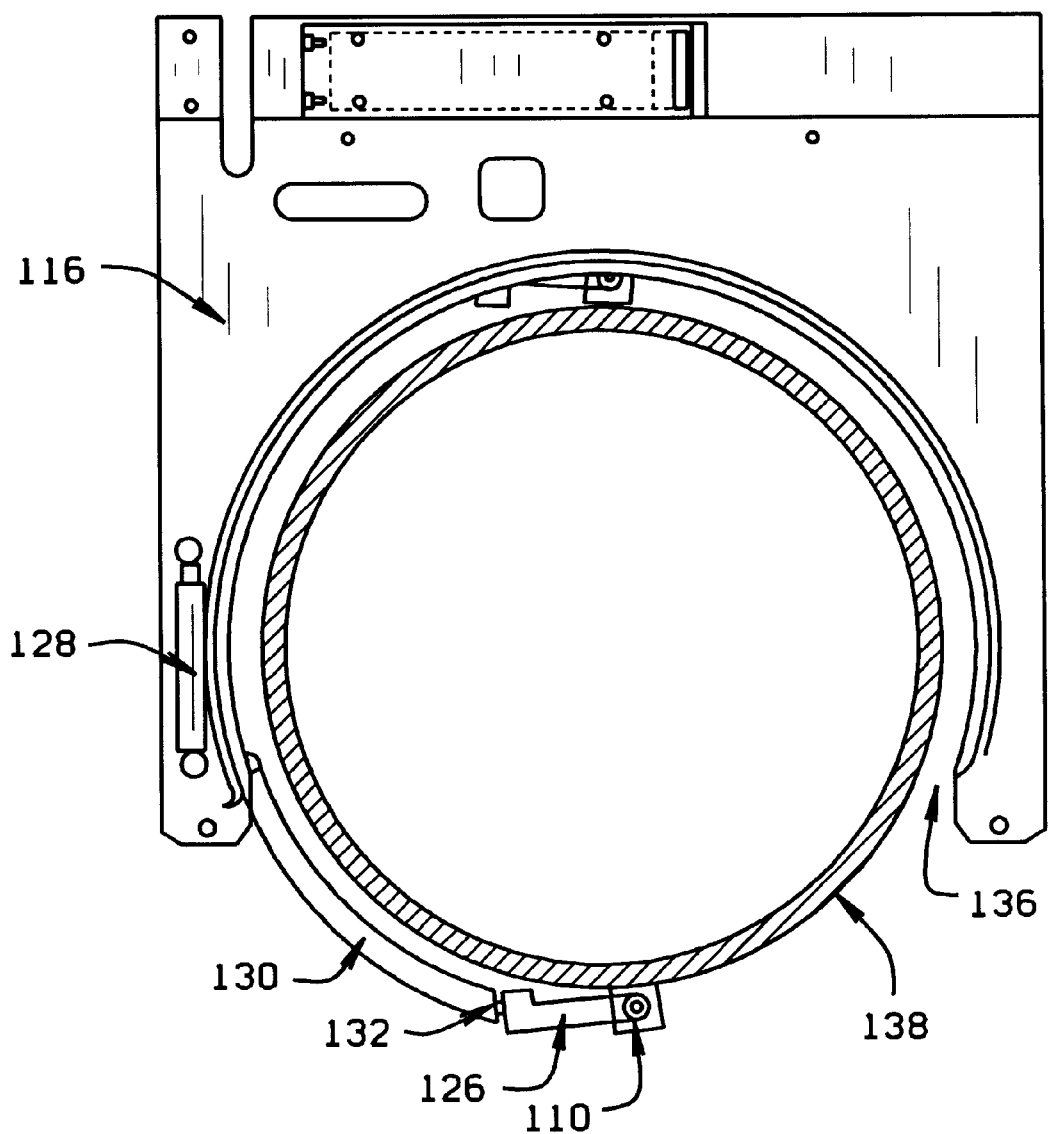
FIG. 4 is a top view of the scan apparatus shown in FIG. 2 along B—B.

FIG. 4 is a top view of scan apparatus 100 showing connector 128, scan platform 116, and arcuate cutout 136. Connector 128 is positioned at an end of its sliding movement and ultrasonic transducers 110 are rotated fully to their rightmost position.

In operation, piping 104 and welds 106 of pipe elbow are inspected using scan apparatus 100 by a method that includes positioning scan head 108 and at least one transducer probe 126 such that at least one ultrasonic transducer 110 is in substantial contact with a pipe elbow surface 138. In one embodiment, there are two transducer probes 126, each holding one ultrasonic transducer 110. Ultrasonic transducers 110 are in substantial contact with pipe elbow surface 138 and are spaced approximately 180 degrees apart.

Scan head 108 is then moved axially along pipe elbow 102 by utilizing motor 112 to pivot ultrasonic transducers 110 substantially about pivot pin 124. This axial movement allows transducer probes 126 to travel axially along pipe elbow 102 while ultrasonic transducers 110 remain in substantial contact with pipe elbow surface 138. The step of moving scan head 108 includes pivoting scan head 108 up to about 90 degrees to accommodate a bend in pipe elbow 102 and to enable scan head 108 to access all pipe elbow surfaces 138. During the axial movement, scan head 108 inspects piping 104 and welds 106 in pipe elbow 102 to detect flaws. Scan apparatus 100 moves with a wrist scan motion to enhance the ability of transducer probes 126 to remain in contact with pipe elbow surface 138 during inspection and to enable ultrasonic transducer signals to better penetrate piping 104 and welds 106 of pipe elbow 102. Piping 104 and welds 106 of pipe elbow 102 are inspected as transducer probes 126 move substantially perpendicular to welds 106.

Figure 5:
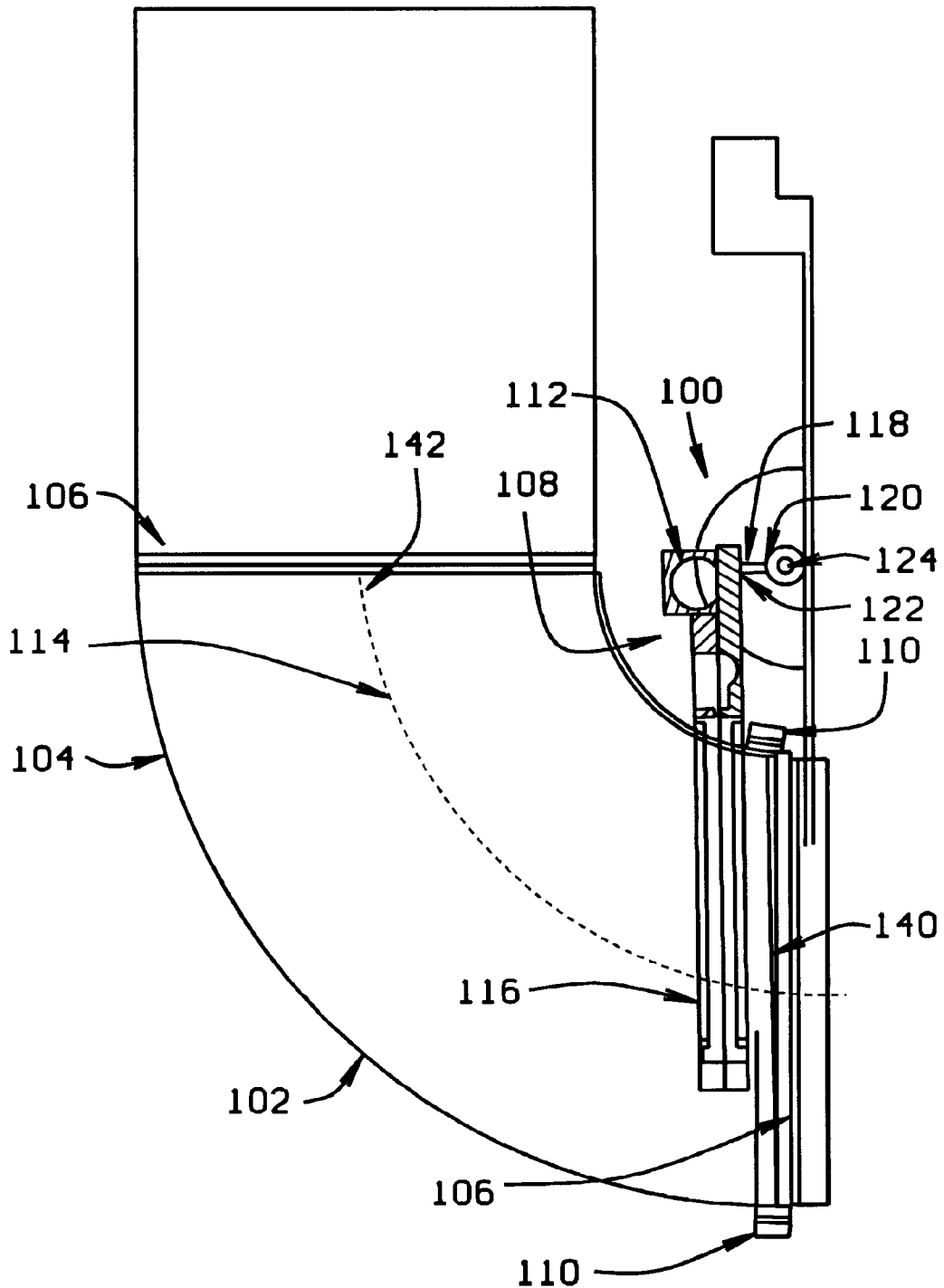
FIG. 5 is a side view of the scan apparatus shown in FIG. 1 after having moved axially along the pipe elbow in a second direction.

FIG. 5 is a side view of a scan apparatus 100 positioned about pipe elbow 102 at a first axial point 140. The axial movement of scan head 108 occurs along pipe elbow 102 in a first direction from first axial point 140 to a second axial point 142. Connector 128 then slides along arcuate cutout 136, incrementally rotating, in a raster type manner, transducer probes 126. Scan head 108 then moves axially along pipe elbow 102 in a second direction from second axial point 142 to first axial point 140. Again, connector 128 slides along cutout 136, incrementally rotating, in a raster type manner, transducer probes 126. Each incremental rotation of transducer probes 126 moves transducer probes 126 about a partial circumference of piping 104. The axial movement of transducer probes 126 and the incremental rotation at the ends of the axial movement are repeated until transducer probes 126 have investigated pipe elbow surface 138 in its entirety.

A method of positioning ultrasonic transducer probes 126 to examine piping 104 and welds 106 of pipe elbow 102 includes locating scan apparatus 100 at pipe elbow 102. Since scan apparatus 100 is for use in a reactor pressure vessel of a boiling water reactor, scan apparatus 100 can be deployed in water to a depth of more than about 60 feet. Scan head 108 is then adjusted to allow at least a portion of piping 104 to enter arcuate cutout 136. The next step includes positioning transducer probes 126 substantially in contact with pipe elbow 102, and moving scan head 108 axially along pipe elbow 102. Transducer probes 126 are maintained in substantial contact with pipe elbow 102 throughout the movement of scan head 108 axially along pipe elbow 102.

The axial movement of pipe elbow 102 begins at first axial point 140 and moves in a first direction to second axial point 142. Connector 128 is then moved incrementally along arcuate cutout 136 which causes transducer probes 126 and transducer arms 130 to rotate partially about a circumference of piping 102. Scan head 108 is then moved axially along pipe elbow 102 in a second direction from second axial point 142 to first axial point 140. Again, connector 128 is moved incrementally along arcuate cutout 136 which causes transducer probes 126 and transducer arms 130 to rotate partially about the circumference of piping 104. The axial movement of transducer probes 126 and the incremental rotation at the completion of the axial movement are repeated until transducer probes 126 have investigated pipe elbow surface 138 in its entirety.

Scan apparatus 100 can be applied to various diameter piping 104 and enables volumetric examination of entire pipe elbows 102. Transducer probes 126 can maintain contact with pipe elbow surface 138 due, at least in part, to the connections between transducer probes 126 and scan platform 116. These connections provide a wrist scan motion that enhances the ability of transducer probes 126 to contour to pipe elbow surface 138 and enables ultrasonic transducer signals to better penetrate pipe elbow surface 138.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method of inspecting piping and welds of a pipe elbow in a reactor pressure vessel of a boiling water reactor using a scan apparatus, the pipe elbow including a surface and the scan apparatus including a scan head having at least one transducer probe including an ultrasonic transducer, at least one transducer arm connected to the transducer probe, a scan platform having an arcuate cutout, a connector connecting the transducer arm to the scan platform, a pivot pin, a pivot arm connecting the scan head to the pivot pin, and a motor capable of moving the scan head axially along the pipe elbow, said method comprising the steps of:

positioning the scan head and the transducer probe such that the ultrasonic transducer is substantially in contact with the pipe elbow surface;

moving the scan head axially along the pipe elbow in a first direction from a first axial point to a second axial point by pivoting the scan head about the pivot pin while maintaining the ultrasonic transducer in substantial contact with the pipe elbow surface;

moving the connector along the arcuate cut out in the scan platform to incrementally rotate the probes circumferentially around the pipe elbow;

moving the scan head axially along the pipe elbow in a second direction from the second axial point to the first axial point by pivoting the scan head about the pivot pin while maintaining the ultrasonic transducer in substantial contact with the pipe elbow surface; and inspecting the piping and the welds in the pipe elbow to detect flaws.

2. A method in accordance with claim 1 wherein the at least one transducer probe includes two transducer probes and wherein said step of positioning the scan head and the ultrasonic transducer probe further comprises the step of positioning two transducer probes in contact with the surface of the pipe elbow approximately 180 degrees apart.

3. A method in accordance with claim 2 wherein the motor is connected to the pivot arm, and wherein the step of moving the scan head further comprises the step of pivoting the ultrasonic transducers, utilizing the motor, substantially about the pivot pin which allows the transducer probes to travel axially along the pipe elbow.

4. A method in accordance with claim 3 wherein the step of moving the scan head further comprises:

moving the transducer probes perpendicular to the weld of the piping; and inspecting the piping and the weld as the transducer probes move substantially perpendicular to the weld.

5. A method in accordance with claim 3 wherein the scan platform includes an arcuate cutout and wherein the step of moving the scan head further comprises moving the connector incrementally along the arcuate cutout to rotate the transducer probes and the transducer arms partially about a circumference of the piping.

6. A method in accordance with claim 1 wherein the step of moving the scan head further comprises the steps of:

moving the scan head axially along the pipe elbow in a first direction from a first axial point to a second axial point by pivoting the scan head about the pivot pin;

incrementally rotating the probes circumferentially around the pipe elbow;

moving the scan head axially along the pipe elbow in a second direction from the second axial point to the first axial point by pivoting the scan head about the pivot pin; and incrementally rotating the probes circumferentially around the pipe elbow.

7. A method in accordance with claim 6 further comprising repeating the method steps of claim 6 until the entire pipe elbow surface has been inspected.

8. A method in accordance with claim 3 wherein the step of moving the scan head further comprises pivoting the scan head up to about 90 degrees to accommodate a bend in the pipe elbow and to enable the scan head to access an upper side of the pipe elbow.

9. A method of positioning ultrasonic transducer probes to examine piping and welds of a pipe elbow in a reactor pressure vessel of a boiling water reactor using a scan apparatus, the scan apparatus including a motor connected to a scan head having at least two ultrasonic transducer probes each including an ultrasonic transducer, a transducer arm connected to each transducer probe, a scan platform having an arcuate cutout, a connector connecting each transducer arm to the scan platform, a pivot pin, and a pivot arm connecting the scan head to the pivot pin, said method comprising the steps of:

locating the scan apparatus at the pipe elbow;

adjusting the scan head to allow at least a portion of the piping to enter the scan platform cutout;

positioning the ultrasonic transducers substantially in contact with the pipe elbow;

moving the scan head axially along the pipe elbow in a first direction from a first axial point to a second axial point by pivoting the scan head about the pivot pin while maintaining the ultrasonic transducers in substantial contact with the pipe elbow;

incrementally rotating the probes circumferentially around the pipe elbow by moving the connector along the arcuate cut out in the scan platform; and moving the scan head axially along the pipe elbow in a second direction from the second axial point to the first axial point by pivoting the scan head about the pivot pin while maintaining the ultrasonic transducer in substantial contact with the pipe elbow surface.

10. A method in accordance with claim 9 wherein the motor is connected to the pivot arm, and wherein the step of moving the scan head further comprises the step of pivoting the ultrasonic transducers, utilizing the motor, substantially about the pivot pin which allows the transducer probes to travel axially along the pipe elbow.

11. A method in accordance with claim 10 wherein the step of moving the scan head further comprises the steps of:

moving the scan head axially along the pipe elbow in a first direction from a first axial point to a second axial point on the piping by pivoting the scan head about the pivot pin;

circumferentially incrementing the connector along the arcuate cutout to incrementally rotate the transducer probes and the transducer arms partially about a circumference of the piping;

moving the scan head axially along the pipe elbow in a second direction from the second axial point to the first axial point on the piping by pivoting the scan head about the pivot pin; and circumferentially incrementing the connector along the arcuate cutout to incrementally rotate the transducer probes and the transducer arms partially about a circumference of the piping.

12. A method in accordance with claim 11 further comprising repeating the method steps of claim 11 until the entire pipe elbow surface has been inspected.

13. A method of inspecting piping and welds of a pipe elbow in a reactor pressure vessel of a boiling water reactor using a scan apparatus, the pipe elbow including a surface and the scan apparatus including a scan head having at least two transducer probes including an ultrasonic transducer, a transducer arm connected to each transducer probe, a scan platform having an arcuate cutout, a connector connecting each transducer arm to the scan platform, a pivot pin, a pivot arm connecting the scan head to the pivot pin and a motor coupled to the scan platform and the pivot arm, said method comprising the steps of:

positioning the scan head and the transducer probe such that the ultrasonic transducer is substantially in contact with the pipe elbow surface;

utilizing the motor, moving the scan head axially along the pipe elbow in a first direction from a first axial point to a second axial point by pivoting the scan head about the pivot pin while maintaining the ultrasonic transducer in substantial contact with the pipe elbow surface;

circumferentially incrementing the connector along the arcuate cutout to incrementally rotate the transducer probes and the transducer arms partially about a circumference of the piping;

moving the scan head axially along the pipe elbow in a second direction from the second axial point to the first axial point by pivoting the scan head about the pivot pin while maintaining the ultrasonic transducer in substantial contact with the pipe elbow surface;

circumferentially incrementing the connector along the arcuate cutout to incrementally rotate the transducer probes and the transducer arms partially about a circumference of the piping; and inspecting the piping and the welds in the pipe elbow to detect flaws.

14. A method in accordance with claim 13 further comprising repeating the method steps of claim 13 until the entire pipe elbow surface has been inspected.

* * * * *